(12) United States Patent
Santangelo

(10) Patent No.: US 8,362,079 B2
(45) Date of Patent: *Jan. 29, 2013

(54) METHOD FOR TREATING HEMODIALYSIS-RELATED OXIDATIVE STRESS USING CYSTINE OR CYSTEINE

(75) Inventor: Francesco Santangelo, Milan (IT)

(73) Assignee: Bio 3 Research S.R.L., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 10/583,334

(22) PCT Filed: Dec. 16, 2004

(86) PCT No.: PCT/EP2004/014359
§ 371 (c)(1),
(2), (4) Date: Mar. 7, 2007

(87) PCT Pub. No.: WO2005/058305
PCT Pub. Date: Jun. 30, 2005

(65) Prior Publication Data
US 2007/0270495 A1 Nov. 22, 2007

(30) Foreign Application Priority Data
Dec. 19, 2003 (IT) .............................. MI2003A2528

(51) Int. Cl.
*A61K 31/198* (2006.01)
(52) U.S. Cl. ....................................... 514/562
(58) Field of Classification Search ................ None
See application file for complete search history.

(56) References Cited

U.S. PATENT DOCUMENTS

| | | | |
|---|---|---|---|
| 4,792,549 A | 12/1988 | Takahashi et al. | |
| 4,794,124 A | 12/1988 | Yamamoto et al. | |
| 4,849,452 A | 7/1989 | Dulce et al. | |
| 5,607,974 A | 3/1997 | Dröge et al. | |
| 6,060,446 A | 5/2000 | Zaloga et al. | |
| 6,627,659 B1 | 9/2003 | Santangelo | |
| 2002/0137785 A1 | 9/2002 | Kindness et al. | |

FOREIGN PATENT DOCUMENTS

| | | |
|---|---|---|
| WO | 93/14750 A | 8/1993 |
| WO | 00/44375 A | 8/2000 |
| WO | 00/53176 A | 9/2000 |
| WO | 02/34303 A | 5/2002 |

OTHER PUBLICATIONS

Sela et al., Kidney International, (59) Suppl. 78 (2001), S159-S163.*
Locatelli et al., Nephrology, Dialysis & Transplantation (2003) 18:1272-1280.*
Atkrui et al., Current Opinion in Pharmacology, (2007), 7:1-5.*
Galli et al., Nephrology, Dialysis, Transplantation (Aug. 2003),18(8), pp. 1592-1600.*
Ross et al., American Journal of Kidney Disease, (Oct. 1997), 30(4), pp. 489-494 (Abstract).*
Ceballos-Picot et al., Free Radical Biology & Medicine, (1996), 21(6), pp. 845-853.*
Database WIP: Sep. 6, 1991: Derwent Publications Ltd.: London, GB: p. 2: AN 1991-306713 XPOO2326744: Funato Toshiaki Et La: "Oral Amino Acid Preparation for Cardiac .Failure".
Database WIP: Aug. 23, 1990: Derwent Publications Ltd.: London, GB: p. 0: AN 1990-301258 XPOO2326745: Ito Tadao: "Hepatopathy Inhibitor".
Moberly James B. et al.: "Elevation of Whole-Body Glutathione in Peritoneal Dialysis . . . (Procysteine)": Journal of the American Society of Nephrology: vol. 9: No. 6: Jun. 1998: pp. 1093-1099: XP008046078: ISSN: 1046-6673.
Bostom A G et al.: "Lack of Effect of Oral N-Acetylcysteine on . . . Patients": Atherosclerosis: Amsterdam, NL: vol. 120: No. 1-2: 1996: pp. 241-244: XP000991283: ISSN: 0021-9150.
M. H. Beers: R. Berkow: "The Merck Manual of Diagnosis and Therapy, Seventeenth Edition": 1999: Merck Research Laboratories: Whitehuse Station N.J.: XP002326823: p. 1841-p. 1848.
Santangelo, F., "Intracellular Thiol Concentration Modulating Inflammatory Response: Influence on the Regulation of Cell Functions Through Cysteine Prodrug Approach," Current Medicinal Chemistry, vol. 10, No. 1, pp. 1241-1253, 2003.

* cited by examiner

*Primary Examiner* — Phyllis G. Spivack
(74) *Attorney, Agent, or Firm* — Lucas & Mercanti, LLP

(57) ABSTRACT

The invention relates to a method and composition for treatment of oxidative stress resulting from hemodialysis treatment in patients suffering from chronic kidney failure or End-Stage Renal Disease by administration of cystine, cysteine or mixtures thereof.

2 Claims, No Drawings

METHOD FOR TREATING HEMODIALYSIS-RELATED OXIDATIVE STRESS USING CYSTINE OR CYSTEINE

This invention relates to the use of cysteine and its disulphide oxidised form (cystine) to prepare oral medicinal products for the prevention and treatment of oxidative stress resulting from haemodialysis treatment in patients suffering from chronic kidney failure.

The invention also relates to the use of cysteine or cystine for the preparation of a medicament for the treatment and prevention of acute or chronic kidney diseases.

BACKGROUND OF THE INVENTION

Oxidative stress is defined as an imbalance between the physiological systems of antioxidant protection and increased production of oxygen or nitrogen radicals by the cells of the immune system. The result can be damage to the molecular structure of proteins, sugars and lipids together with damage to the cell functions, which also prejudices the functions of the body's vital organs. Oxidative stress has been observed to be particularly evident in patients suffering from kidney failure and undergoing haemodialysis. This phenomenon is attributed to bioincompatibility between the patient's circulating blood cells and the dialysis membranes, together with other factors such as a chronic uraemic state. This bioincompatibility leads to excessive production of Reactive Oxygen Species (ROS) by the immune system, and at the same time a reduction in the antioxidant capacity of the body due to losses of antioxidant molecules such as glutathione (GSH), vitamin A, vitamin C and vitamin E through the filters of the dialysis membranes.

One of the consequences of this abnormal immune response is a condition of oxidative stress, which leads to greater susceptibility to infection due to the defective immune response, amyloidosis and accelerated atherosclerosis due to continual activation of the immunocompetent cells. This triggers an inflammatory response, with consequent continual release of cytokines and lysosomal proteolytic enzymes, and stimulation of free radical production; in practice the oxidative stress becomes a self-replicating process, and generates a condition of chronic inflammation.

The main consequence of oxidative stress is cardiovascular complications, which are the main cause of death in patients suffering from chronic kidney failure. At local level these complications are manifested by alterations of the endothelium, accumulation of lipids, formation of clots and occlusion of the lumen.

At systemic level, chronic oxidative stress stimulates acute-phase protein synthesis by the liver at the expense of synthesis of other proteins, such as albumin and transferrin: the result is malnutrition, which is exacerbated by catabolic breakdown of muscle proteins and reduced appetite.

The chronic renal failure (CRF) is a progressive disease of kidney; when the kidney has lost all its ability of clear the blood, the patients cannot survive and have to be submitted to the dialysis procedure. Such a last condition is defined End-Stage Renal-Disease (ESRD).

Examples of the treatment of oxidative stress by administering products with antioxidant activity are reported below. The product most often used for the prevention and treatment of oxidative stress at present is N-acetylcysteine (see, for example, Kidney Int., Vol 64 (2003), pp. 82-91; *Current Med. Chem.*, 2003, 10, pp. 1241-53). In particular, WO 01/02004 describes the use of N-acetylcysteine by intravenous injection before and/or during haemodialysis treatment.

According to Nakanishi et al., *Kidney Int.* 2003 March; 63(3): 1137-40, the plasma concentration of cysteine and homocysteine increases in patients with chronic kidney failure who undergo dialysis. It consequently does not seem logical to further increase the cysteine concentration in these patients.

Santangelo F., *Current Med. Chem.*, 2003, 10, 2599-2610, has recently reviewed the therapeutic uses of cysteine pro-drugs such as N-acetylcysteine and its esters, thiazolidines, γ-glutamylcysteine and glutathione esters, particularly discussing the importance of intracellular GSH concentration. The oral administration of cysteine or cystine rather than derivatives thereof has been however neither disclosed nor suggested by this review.

DESCRIPTION OF THE INVENTION

The present invention involves the administration of cystine and/or cysteine for the prevention and treatment of oxidative stress resulting from haemodialysis treatment in patients suffering from chronic kidney failure.

According to a further embodiment, the invention also concerns the use of cystine and/or cysteine for the preparation of a medicament to be administered by the oral route for the treatment and prevention of chronic or acute kidney diseases as well as for the treatment and prevention of End-Stage renal Disease (ESRD).

The use of cysteine is preferred, but other substances known to have antioxidant properties, such as taurine, lipoic acid, and vitamins A, C and E, could also be added.

This invention therefore relates to oral compositions containing cystine and/or cysteine for the prevention and treatment of oxidative stress resulting from haemodialysis treatment in patients suffering from chronic kidney failure or for the treatment and prevention of acute or chronic kidney diseases or for the treatment and prevention of End-Stage renal Disease (ESRD).

These compositions will be prepared according to conventional methods well known in pharmaceutical technology, such as those described in "Remington's Pharmaceutical Handbook", Mack Publishing Co., N.Y., USA.

This invention involves the oral administration of an effective quantity of cystine and/or cysteine before and/or after haemodialysis treatment in patients suffering from kidney failure. This quantity will depend on various factors, such as the severity of the condition and the patient's weight. However, a unit dose will generally contain 200 to 1000 mg of cystine and/or cysteine. The compositions according to the invention will normally be administered before and/or after the haemodialysis treatment. These compositions are preferably administered in the form of compositions with an oral unit dose.

For the treatment and prevention of acute or chronic kidney diseases or for the treatment and prevention of End-Stage renal Disease (ESRD), the effective dose of cysteine or cystine ranges from 100 to 1000 mg, from 1 to 4 times a day.

According to a further aspect of the invention, the cystine or cysteine can be associated with non-toxic oral antioxidants, in particular vitamins A, C and E, lycopene, lipoic acid, ascorbic acid and taurine. Vitamin E and taurine are preferred.

According to the invention, the compositions may be in the form of tablets, capsules, oral preparations, powders, granules, lozenges, reconstitutable powders, syrups, solutions or suspensions. The solid compositions may contain conventional excipients, for example binders such as cellulose, mannitol and lactose; diluents, such as calcium carbonate, calcium phosphate and lactose; compression agents; lubricants such as magnesium stearate; disintegrants such as starch, polyvinylpyrrolidone and starch derivatives; colorants; flavouring agents and the like.

The liquid compositions may contain conventional excipients, for example suspending agents such as sorbitol, methylcellulose, hydroxyethylcellulose and carboxymethylcellulose; preservatives, for example methyl or propyl p-hydroxybenzoate or sorbic acid, and conventional flavouring agents or colorants if desired.

The oral administration of cystine and/or cysteine offers considerable advantages in terms of cost, ease and safety of administration compared with the use of intravenous and/or infusion formulations of N-acetylcysteine, which require skilled personnel for administration before dialysis treatment, and also involve the risk of contamination during dialysis.

The invention claimed is:

1. A method of treating oxidative stress resulting from hemodialysis in a patient undergoing hemodialysis consisting of subjecting said patient to hemodialysis and before, after or both before and after said hemodialysis treatment consisting of administering orally a dose of cysteine, cystine or a mixture of both to said patient.

2. Method as claimed in claim 1, wherein the cystine and/or cysteine is administered in unit doses ranging from 200 to 1000 mg.

* * * * *